US009897603B1

(12) United States Patent
Acosta et al.

(10) Patent No.: US 9,897,603 B1
(45) Date of Patent: Feb. 20, 2018

(54) NANODIAMOND COUNTING

(71) Applicant: Verily Life Sciences LLC, Mountain View, CA (US)

(72) Inventors: Victor Marcel Acosta, San Francisco, CA (US); Jerrod Schwartz, San Francisco, CA (US); Vasiliki Demas, San Jose, CA (US); Vikram Singh Bajaj, Mountain View, CA (US); Jason Donald Thompson, Palo Alto, CA (US); Mark West Askew, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/652,665

(22) Filed: Jul. 18, 2017

Related U.S. Application Data

(63) Continuation of application No. 14/336,589, filed on Jul. 21, 2014, now Pat. No. 9,759,719.

(51) Int. Cl.
 *G01N 33/569* (2006.01)
 *G01N 33/543* (2006.01)
(52) U.S. Cl.
 CPC ......... *G01N 33/569* (2013.01); *G01N 33/543* (2013.01)
(58) Field of Classification Search
 None
 See application file for complete search history.

(56) References Cited

U.S. PATENT DOCUMENTS

| 6,171,780 B1 | 1/2001 | Pham et al. |
| 2008/0226562 A1 | 9/2008 | Groves et al. |
| 2009/0011403 A1 | 1/2009 | Smith et al. |

(Continued)

FOREIGN PATENT DOCUMENTS

| EP | 2053134 A2 | 4/2009 |
| WO | 2013066446 A1 | 5/2013 |

OTHER PUBLICATIONS

Sarkar et al., Wide-field in vivo background free imaging by selective magnetic modulation of nanodiamond fluorescence., Biomedical Optics Express, vol. 5, No. 4, published Mar. 14, 2014, pp. 1190-1202.

(Continued)

*Primary Examiner* — Rebecca L Martinez
(74) *Attorney, Agent, or Firm* — McDonnell Boehnen Hulbert & Berghoff LLP

(57) ABSTRACT

Methods and systems for detecting the locations of individual instances of an analyte (e.g., individual cells, individual molecules) in an environment are provided. The environment includes functionalized fluorophores that are configured to selective interact with (e.g., bind with) the analyte and that have a fluorescent property that can be modulated (e.g., a fluorescence intensity that can be affected by the presence of a magnetic field). Detecting the location of individual instances of the analyte includes illuminating the environment and detecting signals emitted from the fluorophores in response to the illumination during first and second periods of time. Detecting the location of individual instances of the analyte further includes modulating the modulatable fluorescent property of the fluorophores during the second period of time and determining which individual fluorophores in the environment are bound to the analyte (Continued)

based on the signals detected during the first and second periods of time.

14 Claims, 8 Drawing Sheets

(56) References Cited

U.S. PATENT DOCUMENTS

| | | |
|---|---|---|
| 2011/0006218 A1 | 1/2011 | Mochalin et al. |
| 2011/0062957 A1 | 3/2011 | Fu et al. |
| 2011/0256528 A1 | 10/2011 | Poetter et al. |
| 2012/0156678 A1 | 6/2012 | Le et al. |
| 2013/0288923 A1 | 10/2013 | Vallee-Belisle et al. |
| 2014/0099007 A1 | 4/2014 | Sarkar et al. |

OTHER PUBLICATIONS

Hui et al., Wide-field imaging and flow cytometric analysis of cancer cells in blood by fluorescent nanodiamond labeling and time gating., Scientific Reports, 4:5574, published Jul. 4, 2014, pp. 1-7.

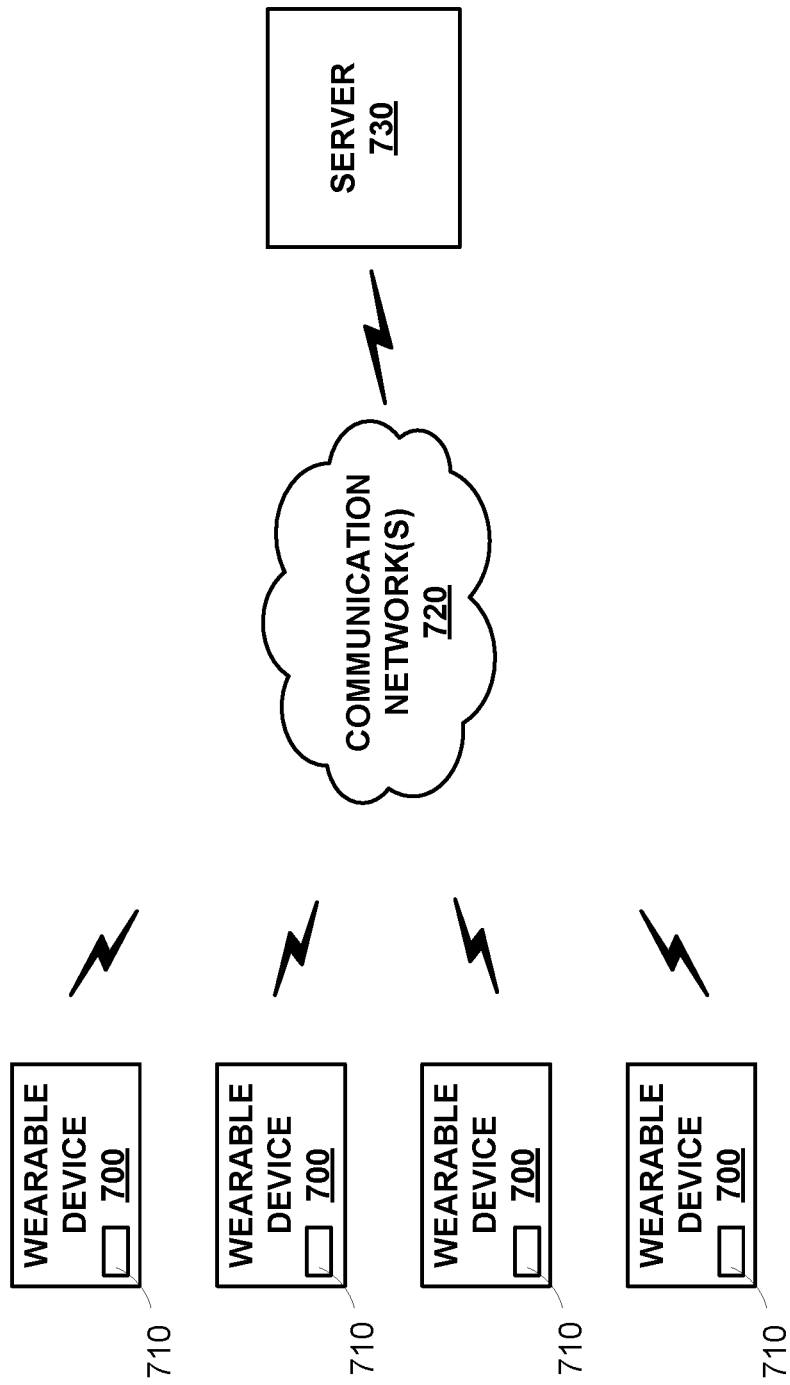

NANODIAMOND COUNTING

CROSS-REFERENCE TO RELATED APPLICATION

This application claims the benefit of and incorporates by reference the content of U.S. Non-Provisional patent application Ser. No. 14/336,589, filed Jul. 21, 2014.

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities of scientific or medical interest. The one or more analytes could be cofactors, substrates, products, or other substances related to a drug under development. The one or more analytes could be present in living or nonliving human or animal tissue, and could be detected and/or measured in an in vivo, ex vivo, in vitro, or some other type of sample. The one or more analytes could include enzymes, reagents, hormones, proteins, cells or other molecules.

Detecting and/or measuring one or more analytes in a biological or other environment can be accomplished through the use of an imaging or contrast agent targeted to the one or more analytes. The contrast agent can facilitate detection and/or measurement of the one or more analytes by having an optical, magnetic, electromagnetic, acoustical, and/or some other property that is detectably different from a surrounding environment. Detection of the targeted contrast agent in the environment could be used as a proxy for detection of the one or more analytes. For example, the contrast agent could absorb light of a first wavelength and emit light of a second wavelength in response to absorbing the light of the first wavelength. The contrast agent could be detected by emitting light of the first wavelength into the environment (e.g., a lumen of vasculature of a person's body) and detecting light of the second wavelength that is emitted from the environment in response to emitting the light of the first wavelength.

SUMMARY

Some embodiments of the present disclosure provide a method including: (i) exposing a detection environment to first illumination during a first period of time, wherein the detection environment includes a plurality of functionalized fluorophores, wherein each of the functionalized fluorophores has a fluorescent property that is modulatable, wherein each of the functionalized fluorophores is functionalized to selectively bind to an analyte, and wherein the first illumination causes individual functionalized fluorophores to emit respective first-period signals; (ii) detecting the first-period signals emitted by the functionalized fluorophores during the first period of time in response to the first illumination; (iii) modulating the modulatable fluorescent property of the functionalized fluorophores during a second period of time; (iv) exposing the detection environment to second illumination during the second period of time, wherein the second illumination causes individual functionalized fluorophores to emit respective second-period signals; (v) detecting the second-period signals emitted by the functionalized fluorophores during the second period of time in response to the second illumination; and (vi) determining which individual functionalized fluorophores are bound to the analyte based at least on the detected first-period signals and the detected second-period signals.

Some embodiments of the present disclosure provide a system including: (i) a light source, wherein the light source is configured to illuminate a detection environment, wherein the detection environment includes a plurality of functionalized fluorophores, wherein each of the functionalized fluorophores has a fluorescent property that is modulatable, wherein each of the functionalized fluorophores is functionalized to selectively bind to an analyte, and wherein illuminating the detection environment causes individual functionalized fluorophores to emit respective light signals; (ii) a light sensor, wherein the light sensor is configured to detect light signals emitted by the functionalized fluorophores in response to illumination by the light source; and (iii) a fluorescence modulator, wherein the fluorescence modulator is configured to modulate the modulatable fluorescent property of the functionalized fluorophores.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a block diagram of an example system that includes a plurality of wearable devices in communication with a server.

DETAILED DESCRIPTION

Figure 1B:
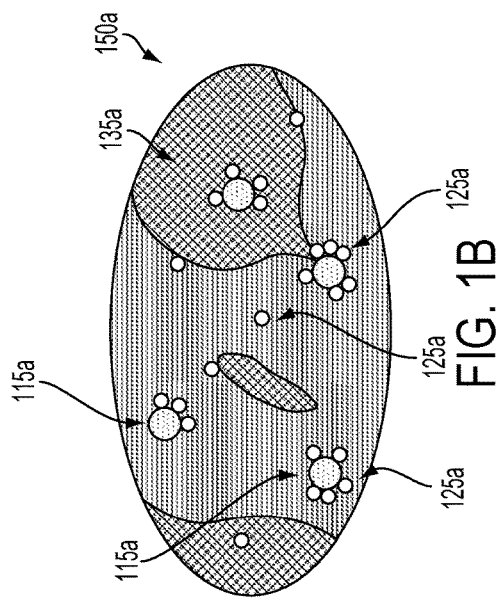
FIG. 1B is an example fluorescent image of the environment shown in FIG. 1A.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a gel, an emulsion, a fluid conduit, a fluid reservoir, etc. For example, one of skill in the art will recognize that the embodiments disclosed herein may be used to sense analytes present in a water treatment system. Moreover, while the present disclosure describes embodiments for use in vivo, one of skill in the art will also recognize that in vitro applications are possible as well. Accordingly, the environment may also include a test tube or other vessel for holding a fluid.

I. Overview

The presence and/or concentration of a low-concentration or otherwise rare analyte in a biological or other environment (e.g., an environment within a human body) could be determined by using a functionalized fluorophore that is configured to selectively interact with the analyte. The functionalized fluorophore is fluorescent (i.e., the functionalized fluorophore emits light in response to being illuminated) and has some fluorescent property that can be modulated to enable detection of individual instances of the functionalized fluorophore and/or individual clusters of the functionalized fluorophore. The environment containing the functionalized fluorophores and the analyte (e.g., an aqueous medium in an in vitro sample container) could be illuminated, and light emitted by the functionalized fluorophores could be detected and used to determine a property (e.g., a count, a concentration) of the analyte. The location or other information about individual functionalized fluorophores could be used to determine the presence, location, count, or other information about the analyte and/or individual instances of the analyte. Location or other information about the functionalized fluorophores in the environment (and thus about the analyte in the environment) could be determined by illuminating the environment and detecting responsively emitted light during a first period of time and then illuminating the environment and detecting responsively emitted light during a second period of time when a fluorescent property of the functionalized fluorophores (e.g., an extinction coefficient, a quantum yield, a lifetime) is modulated (e.g., by exposing the environment to microwave radiation) by some source of fluorescence modulation (e.g., a microwave emitter).

The functionalized fluorophore could include a variety of light-emitting elements, including but not limited to fluorescent chemicals, color-center-doped nanodiamonds (e.g., nitrogen-vacancy-containing nanodiamonds), quantum dots, Raman dyes, and electric field sensitive dyes. Individual color centers (for example, negatively-charged nitrogen vacancy centers, sometimes referred to as nitrogen vacancy color centers, nitrogen vacancy defects, or nitrogen color centers) in diamond can be illuminated (e.g., from about 500 nanometers to about 650 nanometers for negatively-charged nitrogen vacancy centers) and can emit light in response to the illumination (e.g., from about 650 nanometers to 800 nanometers for negatively-charged nitrogen vacancy centers). One or more properties of light emitted in response to illumination by individual color centers in the functionalized nanodiamonds or other fluorescent elements of the functionalized fluorophores could be related to a polarization of the illumination, a magnetic or electric field or electromagnetic energy present in the environment of the functionalized fluorophores, or some other source of modulation. The functionalized fluorophores could be functionalized with receptors, proteins, antibodies, DNA sequences, and/or other materials such that the functionalized fluorophores selectively interact with the analyte, allowing the presence of the analyte to be inferred based on determined locations, aggregation, motions, or other properties of functionalized fluorophores in the environment.

The analyte and/or functionalized fluorophore could be extracted from a source environment and introduced into a detection environment (e.g., an in vitro sample container) that is proximate to a light source, a fluorescence modulation source, and a light sensor. For example, a blood sample containing the analyte (e.g., cancer cells) could be extracted from a human and introduced into a sample medium that contains the functionalized fluorophores. The sample medium and/or a sample container or other vessel containing the sample medium could be configured to present the sample medium, analyte, and functionalized fluorophores to the light source and light sensor in the form of a substantially planar region, such that the light sensor (e.g., a high-resolution camera) could be operated to generate one or more images of the substantially planar region that could be used to determine the location, aggregation, motions, concentration, or other properties of functionalized fluorophores and/or the analyte in the detection environment. A thickness of the substantially planar region containing the sample medium, analyte, and functionalized fluorophores could be a specified thickness such that individual functionalized fluorophores could be imaged with substantially no overlap.

A property of the fluorescence of the functionalized fluorophores could be modulated to enable detection of the location or other properties of the functionalized fluorophores in the environment. For example, the environment could be imaged (i.e., illuminated, and light responsively emitted by the functionalized fluorophores detected) during two time periods, with a fluorescence property of the functionalized fluorophores modulated (e.g., a fluorescence intensity decreased) during one of the time periods. A difference in the images generated during the first and second time periods could be related to light emitted by the functionalized fluorophores rather than by other fluorescent elements of the environment. The nature of the fluorescence modulation could be related to a property of the functionalized fluorophore. In examples where the functionalized fluorophore contains a nitrogen-vacancy color center, modulation could include changing a direction of polarization of the illumination, exposing the environment to microwave radiation, exposing the environment to a high-strength magnetic field, or exposing the environment to some other energy, field, or other condition or combination of conditions such that a fluorescent property or state of the nitrogen-vacancy color centers is modulated. In examples where the functionalized fluorophore contains a quantum dot, modulation could include changing a direction of polarization of the illumination, exposing the environment to an electric field, or exposing the environment to some other energy, field, or other condition or combination of conditions such that a fluorescent property or state of the quantum dots is modulated. Additional and alternative fluorophores and corresponding types of fluorescence modulation and delivery thereof are anticipated.

The functionalized fluorophores can be functionalized by covalently or otherwise attaching or associating a bioreceptor that specifically binds or otherwise interacts with a particular analyte or portion of a particular analyte. The bioreceptor can be an antibody, peptide, nucleic acid, phage, bacteria, virus, aptamer or any other molecule with a defined affinity for a target analyte. Other compounds or molecules, such as fluorophores or autofluorescent or luminescent markers or non-optical contrast agents (e.g. acoustic impedance contrast, RF contrast and the like), which may assist in interrogating the functionalized fluorophores may also be attached to the functionalized fluorophores.

The functionalized fluorophores could include other elements in addition to those described herein. Those of skill in the art will understand a "particle" in its broadest sense and that it may take the form of any fabricated material, a molecule, cryptophan, a conductive or nonconductive nanorod, a quantum dot, a virus, a phage, a complex of nanodiamonds, etc. Further, a particle may be of any shape, for example, spheres, rods, non-symmetrical shapes, etc.

A system may include one or more data collection systems for interrogating functionalized fluorophores and analytes present in an environment, such as an in vitro sample container. In some examples, the system may include an interrogating light source for transmitting illumination that can penetrate into the environment, a fluorescence modulator configured to modulate a property of the fluorescence of the functionalized fluorophores in the environment, and a light sensor for detecting an emitted light that is emitted by the functionalized fluorophores in the environment in response to the illumination. The emitted light can have one or more properties that are dependent on modulation of a fluorescent property of the functionalized fluorophores by the fluorescence modulator, such that the location, relative motion, or other properties of the functionalized fluorophores can be detected by illuminating and detecting responsively emitted light from the functionalized fluorophores during a first period of time when the fluorescent property is not modulated and a during a second period of time when the fluorescent property is modulated. The fluorescence modulator may be configured to emit one or more of magnetic fields, radiofrequency electromagnetic radiation, microwave radiation, or some other directed electric or magnetic phenomenon. Additionally or alternatively, the fluorescence of the functionalized fluorophores could be modulated by changing a property of the illumination, e.g., by changing a direction and/or degree of polarization of illumination emitted by the light source.

It should be understood that the above embodiments, and other embodiments described herein, are provided for explanatory purposes, and are not intended to be limiting.

The analyte could be any analyte of interest, including analytes indicative of, causative of, or otherwise related to a medical condition of a human whose body contains the analyte and/or whose body contains a concentration of the analyte within a certain range of concentrations. Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Imaging Agents

In some examples, information about analytes in an environment can be obtained by detecting properties of an imaging agent, for example, functionalized fluorophores as described herein. Functionalized fluorophores can include a variety of fluorescent (i.e., configured to emit light in response to illumination) chemicals, molecules, proteins, moieties, crystals, layered semiconductor structures, color-center-doped nanodiamonds (e.g., nitrogen-vacancy-containing nanodiamonds), quantum dots, quantum plates, electric field sensitive dyes, or other elements having at least one fluorescent property (e.g., a fluorescence intensity, an extinction coefficient, a fluorescence lifetime, a quantum yield, an emission and/or absorption spectrum) that is modulatable (i.e., that can be changed by some effect in (e.g., an electromagnetic field, a pH, a polarization of the illumination) or contents of (e.g., a chemical) the environment of the functionalized fluorophore. Further, the functionalized fluorophores can be configured to reversibly or irreversibly bind to, conjugate with, or otherwise selectively interact with an analyte by including one or more of a variety of receptors, molecules, proteins, antibodies, DNA or RNA sequences, moieties, aptamers, or other elements.

In some examples, a fluorophore of a functionalized fluorophore could include one or more nanodiamonds containing one or more color centers. Color centers in nanodiamond can emit light in response to illumination of the color centers; further, one or more properties of the emitted light could be related to a magnetic field, electromagnetic oscillation, or other effect in the environment of the color centers. Nanodiamonds can include a variety of color centers. Color centers include dopants that can emit light in response to illumination of the dopants. Color centers can have specific optical properties that make them useful for imaging or use in imaging agents; for example, color centers in nanodiamonds can have narrow light emission spectra. Color center dopants can include a variety of carbon and non-carbon atoms, a variety of crystal defects, and combinations of atoms and defects. For example, a color center in a nanodiamond could include a negatively-charged, positively-charged, multiply-charged, or neutral silicon or nitrogen vacancy center. Individual nanodiamonds could include single color centers or could include populations of color centers. In some examples, the color centers could have orientation-specific properties. For example, negatively-charged nitrogen vacancy centers could be sensitive to magnetic fields parallel to a direction of the nitrogen vacancy center, but substantially insensitive to magnetic fields perpendicular to the direction of the nitrogen vacancy center. A population of color centers in an individual nanodiamond could be randomly oriented, could have a common orientation, or could have some other relationship between the orientations of respective individual color centers of the population of color centers.

Color centers in a nanodiamond could include negatively charged nitrogen vacancy centers. Negatively-charged nitrogen vacancy centers in diamond (NV centers) can be characterized by emission of light having a band of wavelengths between approximately 650 and 800 nanometers. This emission can occur in response to illumination having any wavelength in a range of wavelengths, for example, from about 500 nanometers to about 650 nanometers. Color centers in nanodiamond could additionally or alternatively include negatively-charged centers, positively-charged centers, neutral centers, or multiply-charged centers. Color centers having different charge states can have different respective optical properties. Further, color centers in diamond could additionally or alternatively include other dopants, including silicon, carbon, nickel, or other elements.

Nanodiamonds that are part of functionalized fluorophores as described herein could be polycrystalline. That is, the nanodiamonds can comprise a plurality of crystal domains. Additionally or alternatively, an individual functionalized fluorophore could include a monocrystalline nanodiamond. In some examples, nanodiamonds can have sizes between approximately 5 nanometers and 5 micrometers. For example, a functionalized fluorophore can include nanodiamonds having a mean size of approximately 35 nanometers. In some examples, the size of the nanodiamonds could be chosen such that magnetic resonance peak of color centers in the nanodiamonds was sufficiently narrow to enable some application. For example, the nanodiamonds could be between 10 and 100 nanometers in diameter Optical properties of color centers in nanodiamond could be related to static and/or changing magnetic fields in the environment of the color centers. For example, a fluorescence intensity of the color centers could be modulated by the presence in the environment of the color centers of electromagnetic energy of one or more specific frequencies. Static magnetic fields could cause a change in the number, relative energy, or other properties of allowed spin or other quantum states of the color centers. Time-carrying magnetic fields could cause a change in the occupancy of spin or other quantum states of the color centers by having a frequency corresponding to an energy difference between two or more spin or other quantum states of the color centers.

An optical property of a color center could be dependent upon the occupancy of the two or more spin or other quantum states of the color centers. For example, certain spin or other quantum states of a color center, when occupied, could be more likely to result in emission of a fluorescent photon when the color center is illuminated than other states of the color center. Thus, an overall fluorescence intensity of a color center could be related to the occupancy of spin or other quantum states of the color center, and thus the overall fluorescence intensity of the color center could be related to (e.g., modulated by) static and/or changing magnetic fields in the environment of the color center. Further, an overall fluorescence intensity of a population of color centers (e.g., a population of color centers contained in a nanodiamond of a functionalized fluorophore) could be related to (i.e., modulated by) static and/or changing magnetic fields in the environment of the population of color centers.

Note that negatively charged nitrogen vacancy color centers (NV-centers) are used herein as an illustrative example of a color center that could be contained in a nanodiamond of a functionalized fluorophore to enable the embodiments described herein. Alternate color centers in diamond are anticipated (e.g., silicon-vacancy color centers, nickel-containing color centers, silicon-carbon color centers).

Color centers can have an optical property (e.g., a fluorescence intensity, a property of light emitted by the color centers in response to illumination) that is related to (i.e., modulated by) one or more properties of the environment of the color centers (e.g., a DC magnetic field, a time-varying magnetic field, a temperature). In some examples, the color center could have an occupancy state of spin or other quantum states of the color center that was affected by (i.e., modulated by) the magnetic property of the environment; further, the occupancy state could be related to an optical property of the color center. In some examples, the occupancy state could be polarized or otherwise altered by being illuminated by illumination having a wavelength in a specified range.

The functionalized fluorophores can be designed to selectively bind or otherwise recognize a particular analyte or set analytes by adhering, adsorbing, or otherwise attaching one or more bioreceptors. For example, the bioreceptors can include a variety of structures, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The bioreceptors (or a combination of bioreceptors) could be chosen to cause the functionalized fluorophores to selectively interact with an analyte that includes a target or targets of the bioreceptors. For example, the bioreceptor could be a bioreceptor that selectively interacts with a protein or other element that is expressed by cancer cells; this can enable the use of the functionalized fluorophores to detect cancer cells.

The functionalized fluorophores can be introduced into a variety of environments by a variety of methods. For example, the functionalized fluorophores can be introduced into a person's blood stream by injection, ingestion, inhalation, transdermally, or in some other manner. The fluorophores could then be interrogated (e.g., illuminated by a system that is additionally configured to detect a responsively emitted light signal from the functionalized fluorophores and to modulate a fluorescent property of the functionalized fluorophores) while in the body of the person to determine one or more properties of the body and/or of the analyte by determining a location, state of binding with the analyte, orientation, or other properties of the functionalized fluorophores. Additionally or alternatively, a sample including the analyte could be extracted from the body and introduced into a detection environment (e.g., a biological sample container). The fluorophores could be included in the sample (e.g., the fluorophores could have been introduced into the body before the sample was extracted, as described above), or could be added to the sample and/or to the detection environment. The functionalized fluorophores could then be interrogated in the detection environment to determine one or more properties of the body and/or of the analyte by determining a location, state of binding with the analyte, orientation, or other properties of the functionalized fluorophores. Alternatively, these methods could be used to determine properties of analytes in and/or extracted from other environments (e.g., an animal body, an environment of an industrial process, an environment of a pharmaceutical process, a natural environment).

Fluorophores and/or particles containing fluorophores can be functionalized by attaching bioreceptors to the fluorophores using a variety of methods. Bioreceptors can be attached to the surface of the fluorophores and/or particles including the fluorophores by covalent bonds, adsorption, electrostatic attraction, Van der Waals forces, or by some other mechanism. The surface of the fluorophores and/or particles containing the fluorophores could be treated or altered to facilitate binding of bioreceptors.

Additionally or alternatively, a coating or other substance could contain the fluorophores and/or particles containing the fluorophores, be bound to the surface of the fluorophores and/or particles containing the fluorophores, or otherwise attach to the fluorophores and/or particles containing the fluorophores such that bioreceptors can be attached to the coating or other substance, such that the bioreceptor is indirectly attached to the fluorophores and/or particles containing the fluorophores. More than one bioreceptor could be attached to the fluorophores and/or particles containing the fluorophores. In some examples, complexes of the same or different bioreceptors could be attached directly or indirectly to the fluorophores and/or particles containing the fluorophores such that the fluorophores and/or particles containing the fluorophores more selectively interacted with a target analyte or target portion of a target analyte.

When an environment contains the analyte, and the functionalized fluorophores are configured to selectively interact with (e.g., 'bind' to) the analyte, an individual functionalized fluorophore that is bound to the analyte could be more likely to be proximate to one or more other functionalized fluorophores that are also bound to the analyte. Thus, the detection and/or determination that an individual functionalized fluorophore is proximate to one or more other functionalized fluorophores could be used to determine that the individual functionalized fluorophore was bound to, proximate to, or otherwise interacting with the analyte. Other properties of the functionalized fluorophores in an environment could be detected and/or determined to determine whether individual functionalized fluorophores are bound to the analyte.

Determining whether individual functionalized fluorophores in the environment are bound to the analyte could include determining the location of individual functionalized fluorophores, and further determining the location of instances of the analyte and/or determining which of the individual functionalized fluorophores are bound to the analyte based on a determined proximity between individual functionalized fluorophores (e.g., unbound functionalized fluorophores could be less likely to be proximate to other unbound functionalized fluorophores, while functionalized fluorophores that are bound to an instance of the analyte are likely to be within a specified distance (e.g., a distance related to a characteristic size of the analyte) of other individual functionalized fluorophores).

Additionally or alternatively, determining whether individual functionalized fluorophores in an environment are bound to the analyte could include determining a degree of blur in one or more images of individual functionalized fluorophores and further determining that an individual functionalized fluorophore is bound to the analyte based on the corresponding determined degree of blur. For example, unbound functionalized fluorophores could have faster characteristic motions in the environment than bound functionalized fluorophores (due, e.g., to a drag, mass, or other property of the analyte) and the faster characteristic motion could cause blurring of a corresponding image of the unbound functionalized fluorophore. Additional methods of determining that individual functionalized fluorophores are bound to the analyte based on light signals emitted from the functionalized fluorophores in response to illumination of an environment are anticipated.

Functionalized fluorophores as described herein may additionally include other elements. Functionalized fluorophores could include biodegradable or non-biodegradable materials. For example, the functionalized fluorophores may include polystyrene. Functionalized fluorophores that include non-biodegradable materials may be provided with a removal means to prevent harmful buildup in a body or other environment. Generally, functionalized fluorophores intended for use in a body may be designed to have a long half-life so that they remain in the vasculature, body fluids, or other environment to enable their use in detecting analytes over an extended period of time.

A plurality of types of functionalized fluorophores functionalized to selectively interact with respective analytes in an environment (e.g., a biological sample in a biological sample container) could be used. For example, an imaging agent could include a first set of functionalized fluorophores functionalized to selectively interact with a first analyte and a second set of functionalized fluorophores functionalized to selectively interact with a second analyte, where the where the first set of functionalized fluorophores is detectably different from the second set (e.g., by containing a different type of fluorophore or by some other method).

The analyte could be a clinically-relevant analyte. A clinically-relevant analyte could be any analyte that, when present or absent, or present at a particular concentration or range of concentrations, in a body and/or in a sample extracted from a body may be indicative of a medical condition or indicative that a medical condition may be imminent. For example, the clinically-relevant analyte could be an enzyme, hormone, protein, cell, or other biological element. In one relevant example, certain protein biomarkers expressed by a cell are known to be predictive of the cell being a cancer cell. By providing functionalized fluorophores functionalized with a bioreceptor that will selectively bind to these target protein biomarkers, interaction with the functionalized fluorophores (e.g., illuminating the functionalized fluorophores, detecting properties of light signals emitted by the functionalized fluorophores, and/or modulating a fluorescent property of the functionalized fluorophores) could be used to determine one or more properties of the cell (e.g., how many cancer cells are in the body, that the cell was a cancer cell, a cancer type of the cell).

The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, a, or some other environment. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

A sample containing the analyte could be extracted from an environment and introduced into a detection environment, and functionalized fluorophores in the detection environment could be interrogated to determine one or more properties of the analyte. In some examples, the detection environment could include additional components to facilitate interrogation. For example, the detection environment could include a fixative configured to reduce motion of instances of the analyte and of functionalized fluorophores bound thereto. In some examples, the fixative could include agarose, PMMA, polystyrene, or some other fixative substance that is compatible with the contents of the sample. The sample containing the analyte and/or some other medium added to the sample and/or the detection environment could be an aqueous medium. In some examples, the detection environment could be a substantially planar region having a specified thickness such that interrogation of the functionalized fluorophores (e.g., imaging light signals emitted by the fluorophores in response to illumination during various periods of time relative to modulation of a fluorescent property of the functionalized fluorophores) could generate sufficient information to determine the location of substantially all individual instances of the analyte in the detection environment based on a determination of which functionalized fluorophores in the detection environment are bound to the analyte. For example, the substantially planar detection environment could have a thickness between approximately 10 microns and approximately 20 microns. Further, a concentration and/or count of the analyte in the detection environment and/or the environment from which the sample was extracted could be determined based on the determined locations of individual instances of the analyte in the detection environment.

Those of skill in the art will understand the term "particle" in its broadest sense and that it may take the form of any fabricated material, a molecule, cryptophan, a virus, a phage, a nanodiamond, a nanorod, a quantum dot, a single-magnetic-domain crystal of a metal, etc. Functionalized fluorophores could be described as particles, or could be incorporated into particles including elements additional to the fluorophores and bioreceptors described herein. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer.

III. Illustrative Methods

Figure 1D:
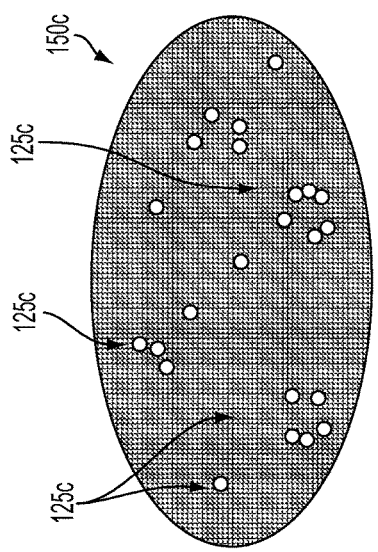
FIG. 1D is an example fluorescence difference image of the environment shown in FIG. 1A.
Figure 1A:
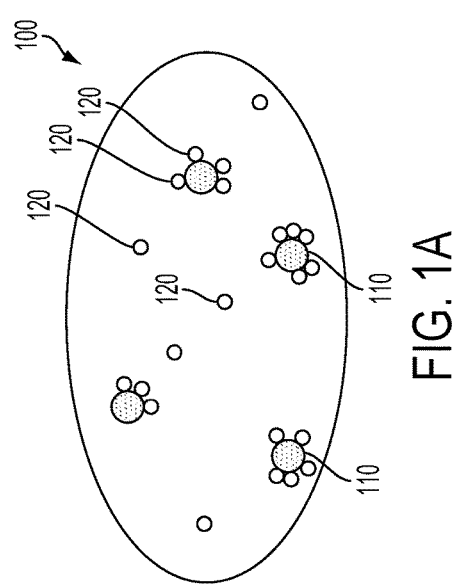
FIG. 1A is an illustration of an example environment containing an analyte and functionalized fluorophores.

FIG. 1A illustrates an example detection environment 100 including an analyte 110 and functionalized fluorophores 120 configured as described herein. The detection environment 100 could be an in vivo or in vitro biological environment, an artificial environment (e.g., an environment of an industrial, pharmaceutical, water or waste treatment, or food preparation process), or an environment containing a sample extracted from some other environment that contains the analyte 110. The functionalized fluorophores 120 could be added to the detection environment 100, added to an environment from which a sample is extracted that contains the analyte 110 and the functionalized fluorophores 120 and that is then introduced into the detection environment 100, or introduced into the detection environment 100 by some other method or process. The detection environment 100 could contain additional elements (not shown), for example, added aqueous or non-aqueous media or solvents, buffers, auto-fluorescent substances, fixatives, buffers, stabilizers, or other substances or elements according to an application.

FIG. 1B illustrates a first fluorescent image 150a of the detection environment 100 generated from first-period light signals emitted by the functionalized fluorophores 120 and other elements of the detection environment 100 during a first period of time in response to exposure of the detection environment 100 to a first illumination during the first period of time. The first fluorescent image 150a includes a first background image 135a corresponding to light signals emitted by background elements of the detection environment (e.g., due to autofluorescence of substances in the detection environment 100, due to scattering of the first illumination, electronic or other noise in an imager used to generate the first fluorescent image 150a, or due to some other process(es)) during the first period of time. The first fluorescent image 150a additionally includes first analyte image 115a corresponding to light signals emitted by the analyte 110 (e.g., due to autofluorescence of the analyte 110 or some other process(es)) during the first period of time. The first fluorescent image 150a additionally includes first fluorophore image 125a corresponding to light signals emitted by the functionalized fluorophore 120 during the first period of time.

Figure 1C:
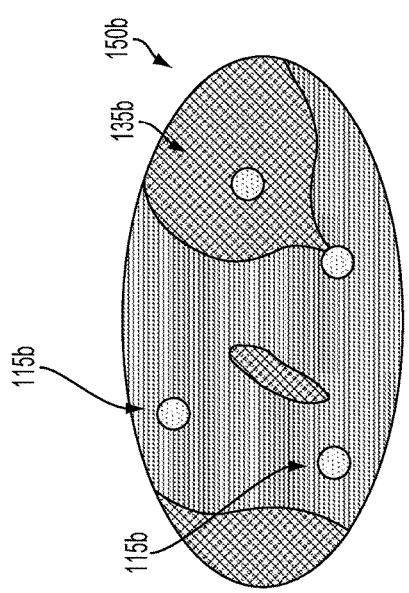
FIG. 1C is an example fluorescent image of the environment shown in FIG. 1A.

FIG. 1C illustrates second fluorescent image 150b of the detection environment 100 generated from second-period light signals emitted by the functionalized fluorophores 120 and other elements of the detection environment 100 during a second period of time in response to exposure of the detection environment 100 to a second illumination during the second period of time. Further, a fluorescence property of the functionalized fluorophores 120 is modulated during the second period of time such that the functionalized fluorophores 120 emit substantially no light in response to the second illumination during the second period of time. The second fluorescent image 150b includes a second background image 135b corresponding to light signals emitted by background elements of the detection environment 100 during the first period of time. The second fluorescent image 150b additionally includes second analyte image 115b corresponding to light signals emitted by the analyte 110 during the second period of time. The second analyte image 115b and second background image 135b are substantially similar to first analyte image 115a and first background image 135a, respectively.

FIG. 1D illustrates a fluorescence difference image 150c. The fluorescence difference image 150c could be generated by subtracting a brightness or other image information of the second fluorescent image 150b from corresponding information of the first fluorescent image 150a. Thus, fluorescence difference image includes a fluorophore difference image 125c related to light signals emitted by the functionalized fluorophore 120 during the first period of time. The location, state of binding with the analyte, orientation, or other properties of the functionalized fluorophores and/or the analyte could be determined based on the fluorophore difference image 125c. For example, a determination of which functionalized fluorophores 120 in the detection environment 100 are bound to the analyte 110 could be determined based on the fluorophore difference image 125c. Such a determination could be used to determine the location of individual instances of the analyte 120 in the detection environment 100 and/or to determine the concentration of the analyte 120 in the detection environment 100. Other information about the analyte 110, the detection environment 100, and the functionalized fluorophores 120 could be determined based on the fluorophore difference image 125c and/or the first-period light signals and the second-period light signals emitted by the functionalized fluorophores during the first and second periods of time, respectively.

Determining which individual functionalized fluorophores 120 in the detection environment 100 are bound to the analyte 110 could include determining the location of individual functionalized fluorophores 120 (e.g., based on the location of bright spots in the fluorophore difference image 125c), and further determining which of the individual functionalized fluorophores 120 are bound to the analyte 110 based on a determined proximity between individual functionalized fluorophores 120. For example, unbound functionalized fluorophores 120 could be less likely to be proximate to other unbound functionalized fluorophores 120, while functionalized fluorophores 120 that are bound to an instance of the analyte 110 are likely to be within a specified distance (e.g., a distance related to a characteristic size of the analyte 120) of other individual functionalized fluorophores 120 in the detection environment 100.

Additionally or alternatively, determining which individual functionalized fluorophores 120 in the detection environment 100 are bound to the analyte 110 could include determining a degree of blur corresponding to individual functionalized fluorophores 120 in one or more images of the environment (e.g., determining a width, mean intensity, or other properties of bright spots in the fluorophore difference image 125c) and further determining that an individual functionalized fluorophore 120 is bound to the analyte 110 based on the corresponding determined degree of blur. For example, unbound functionalized fluorophores 120 could have faster characteristic motions in the detection environment 100 than bound functionalized fluorophores 120 (due, e.g., to a drag, mass, or other property of the bound analyte 110) and the faster characteristic motion could cause blurring of a corresponding image of the unbound functionalized fluorophore 120. Additional methods of determining which individual functionalized fluorophores 120 in the detection environment 100 are bound to the analyte 110 based on light signals emitted from the functionalized fluorophores 120 during two or more periods of time in response to illumination of the detection environment 100 are anticipated.

Figure 2:
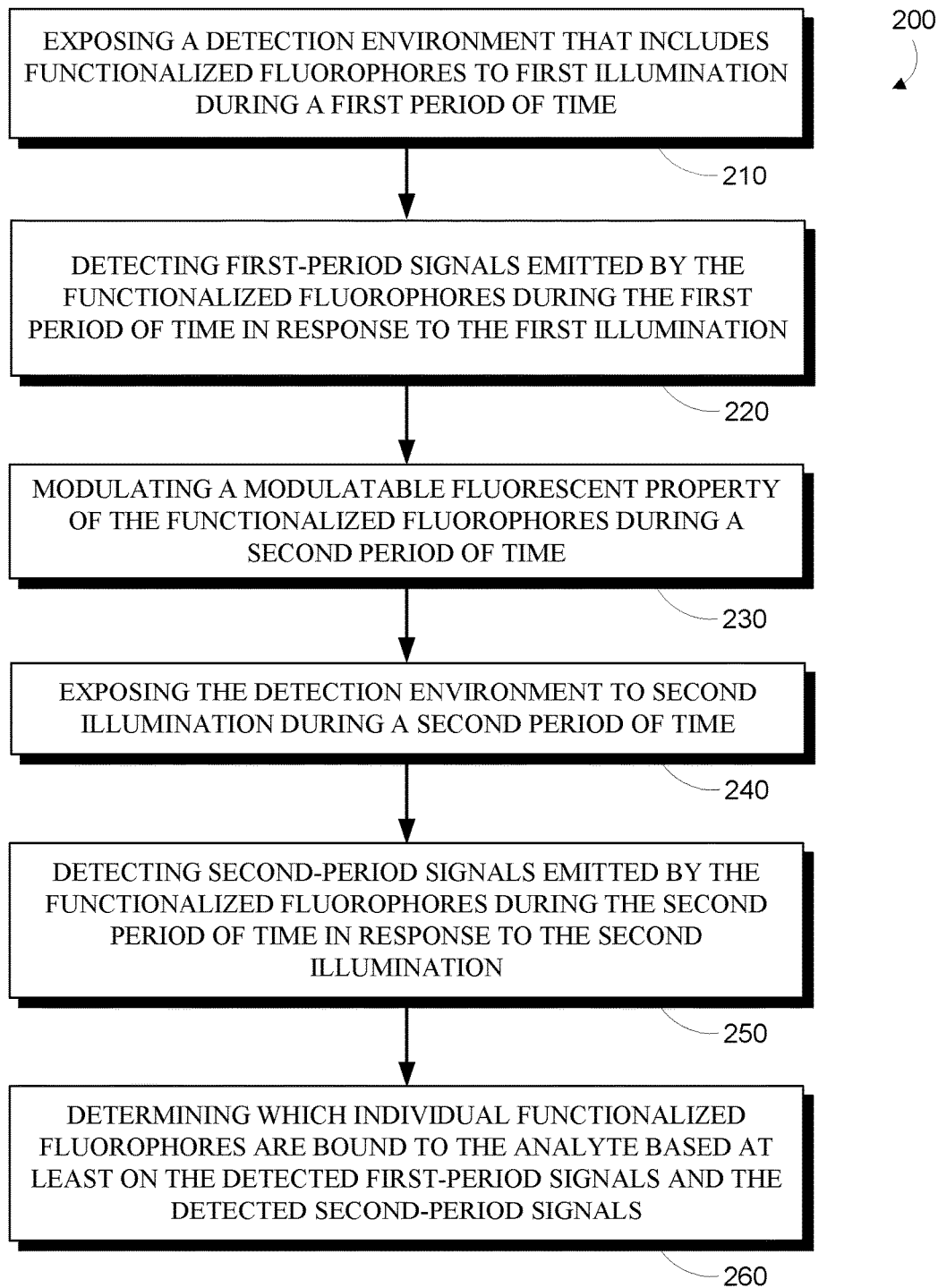
FIG. 2 is a flowchart of an example method.

FIG. 2 is a flowchart of a method 200 for determining which individual functionalized fluorophores in a detection environment are bound to an analyte in the detection environment. Each functionalized fluorophore is configured to selectively interact with the analyte (e.g., by binding to one or more proteins, ligands, or other elements of the analyte). Each functionalized fluorophore has a fluorescent property that is modulatable. That is, one or more properties of fluorescence of the functionalized fluorophore (e.g., a fluorescence intensity, an extinction coefficient, a fluorescence lifetime, a quantum efficiency, an emission and/or absorption spectrum, or some other fluorescent property) can be modulated by an energy, a field, a substance, a temperature, a substance, or some other effect present in the detection environment. For example, a fluorescence intensity of the functionalized fluorophores could be reduced when the detection environment is exposed to microwave radiation. Determining which individual functionalized fluorophores in a detection environment are bound to an analyte in the detection environment could be performed to determine one or more properties (e.g., a concentration of the analyte in the detection environment, a count of individual instances of the analyte in the detection environment) of the analyte and/or the detection environment based on the determined set of individual functionalized fluorophores that are bound to the analyte.

The method 200 includes exposing the detection environment to first illumination during a first period of time 210 such that the functionalized fluorophores emit respective first-period signals in response to the first illumination. Exposing the environment to the first illumination 210 can include emitting first illumination having a specified amplitude, phase, polarization, or other property. Exposing the environment to the first illumination 210 can include emitting first illumination having a specified wavelength or spectral profile corresponding to an absorption spectrum of the functionalized fluorophore. For example, the functionalized fluorophore could include one or more nanodiamonds containing at least one nitrogen-vacancy defect, and the first illumination could include light having a wavelength between approximately 500 nanometers and approximately 650 nanometers.

The first period of time could have a specified duration. For example, the first period of time could have a duration specified relative to an exposure time of an imager configure to image the detection environment during the first period of time. For example, the duration could correspond to an exposure time of approximately 100 milliseconds. The exposure time could be related to an amplitude of the first-period signals, e.g., the exposure time could be a sufficiently long period of time that a corresponding image generated by the imager could be used to determine the location, orientation, state of binding to the analyte, degree of motion, or some other information about the functionalized fluorophores could be determined.

The method 200 includes detecting the first-period signals emitted by the functionalized fluorophores during the first period of time in response to the first illumination 220. Detecting the first-period signals 220 could include operating a light sensor to detect one or more properties of the first period signals (e.g., an intensity, a color, a polarization). Detecting the first-period signals 220 could include generating an image of the detection environment based on the first period signals, e.g., using a camera, a CCD, an array of active pixel sensors, or some other imaging apparatus. Detecting the first-period signals 250 could include detecting light from the detection environment having wavelengths within a specified range of wavelengths corresponding to an emission wavelength or spectral profile of the functionalized fluorophore. For example, the functionalized fluorophore could include one or more nanodiamonds containing at least one nitrogen-vacancy defect, and detecting the first-period signals 250 could include detecting light having wavelengths between approximately 650 nanometers and approximately 800 nanometers.

The method 200 includes modulating the modulatable fluorescent property of the functionalized fluorophores during a second period of time 230. Modulating the modulatable fluorescent property of the functionalized fluorophores 230 could include exposing the detection environment to an electric, a magnetic, and/or an electromagnetic field, exposing the detection environment to ultraviolet, visible, and/or infrared light, controlling a temperature of the detection environment, exposing the detection environment to acoustic waves, exposing the detection environment to a shear force, or exposing the detection environment to some other energy, field, or substance according to the configuration of the functionalized fluorophores.

The second period of time could have a specified duration. For example, the second period of time could have a duration specified relative to an exposure time of an imager configure to image the detection environment during the second period of time. In some examples wherein the first illumination and a second illumination (below) have substantially the same properties, the duration of the second period of time could be substantially the same as the duration of the first period of time such that images of the detection environment taken during the first and second periods of time could be substantially the same, excepting differences corresponding to differences in the first-period signals and second-period signals emitted by the functionalized fluorophores in response to the first and second illumination, respectively.

The method 200 includes exposing the detection environment to second illumination during the second period of time 240 such that the functionalized fluorophores emit respective second-period signals in response to the second illumination. Exposing the environment to the second illumination 240 can include emitting second illumination having a specified amplitude, phase, polarization, or other property. In some examples, the second illumination and the first illumination could have specified properties that are substantially the same. In some examples, a polarization direction of the second illumination could be substantially different from a polarization direction the first illumination. Exposing the environment to the second illumination 240 can include emitting second illumination having a specified wavelength or spectral profile corresponding to an absorption spectrum of the functionalized fluorophore. For example, the functionalized fluorophore could include one or more nanodiamonds containing at least one nitrogen-vacancy defect, and the second illumination could include light having a wavelength between approximately 500 nanometers and approximately 650 nanometers.

The method 200 includes detecting the second-period signals emitted by the functionalized fluorophores during the second period of time in response to the second illumination 250. Detecting the second-period signals 250 could include operating a light sensor to detect one or more properties of the second period signals (e.g., an intensity, a color, a polarization). Detecting the second-period signals 250 could include generating an image of the detection environment based on the second period signals, e.g., using a camera, a CCD, an array of active pixel sensors, or some other imaging apparatus. In some examples, detecting the second-period signals 250 could include operating the same light sensor or other detector used to detect the first-period signals in substantially the same manner as the light sensor or other detector is operated during the first time period. Detecting the second-period signals 250 could include detecting light from the detection environment having wavelengths within a specified range of wavelengths corresponding to an emission wavelength or spectral profile of the functionalized fluorophore. For example, the functionalized fluorophore could include one or more nanodiamonds containing at least one nitrogen-vacancy defect, and detecting the second-period signals 250 could include detecting light having wavelengths between approximately 650 nanometers and approximately 800 nanometers.

The method 200 includes determining which individual functionalized fluorophores are bound to the analyte based at least on the detected first-period signals and the detected second-period signals 260. Determining which individual functionalized fluorophores are bound to the analyte 260 could include making a determination based on a difference between the detected first-period signals and the detected second-period signals. For example, determining which individual functionalized fluorophores are bound to the analyte 260 could include generating a difference image between a first fluorescence image of the detection environment related to the detected first-period signals and a second fluorescence image of the detection environment related to the detected second-period signals. The generated difference image could correspond to differences between the first-period signals and the second-period signals related modulating the modulatable fluorescent property of the functionalized fluorophores during the second period of time 230. For example, modulating the modulatable fluorescent property of the functionalized fluorophores 230 could cause the second-period signals to have a significantly smaller amplitude than the first-period signals. As a result, the generated difference image could be an image related to the locations, motions, states of binding with the analyte, orientations, or other properties of the functionalized fluorophores and/or the analyte in the detection environment.

Determining which individual functionalized fluorophores are bound to the analyte 260 could include determining the location of individual functionalized fluorophores based on the detected first- and second-period signals, and further determining the location of instances of the analyte and/or determining which of the individual functionalized fluorophores are bound to the analyte based on a determined proximity between individual functionalized fluorophores. For example, unbound functionalized fluorophores could be less likely to be proximate to other unbound functionalized fluorophores, while functionalized fluorophores that are bound to an instance of the analyte are likely to be within a specified distance (e.g., a distance related to a characteristic size of the analyte) of other individual functionalized fluorophores.

Additionally or alternatively, determining which individual functionalized fluorophores are bound to the analyte 260 could include determining a degree of blur in one or more images (i.e., images related to the detected first- and second-period signals, a difference image) of individual functionalized fluorophores and further determining that an individual functionalized fluorophore is bound to the analyte based on the corresponding determined degree of blur. For example, unbound functionalized fluorophores could have faster characteristic motions in the environment than bound functionalized fluorophores (due, e.g., to a drag, mass, or other property of the analyte) and the faster characteristic motion could cause blurring of a corresponding image of the unbound functionalized fluorophore. An exposure time used to detect the first- and second-period signals (e.g., an exposure time of a camera, light sensor, or other imaging apparatus) could be specified such that images exhibit a detectably different amount of blur between images of functionalized fluorophores that are bound to the analyte and images of functionalized fluorophores that are not bound to the analyte. A degree of blur could be determined based on a width, a mean amplitude or intensity, a shape, a degree of distortion, or some other property of elements of an image (e.g., bright spots of a difference image) corresponding to individual functionalized fluorophores in the detection environment. Additional or alternatively calculations, methods, or other steps relating to determining which individual functionalized fluorophores are bound to the analyte 260 are anticipated.

The method 200 could include additional steps. The method 200 could include extracting a sample containing the analyte from a living body (e.g., from blood in a lumen of vasculature of a body) or from some other environment of interest and introducing the extracted sample into the detection environment that is external to the living body or other environment or interest. For example, a blood sample containing the analyte (e.g., cancer cells) could be extracted from a human and introduced into a detection environment (e.g., a sample container) that contains the functionalized fluorophores. The detection environment could be configured to present the sample, the analyte, and functionalized fluorophores to a light source configured to emit the first and second illumination and to light sensor configured to detect the first- and second-period signals in the form of a substantially planar region, such that the light sensor (e.g., a high-resolution camera) could be operated to generate one or more images of the substantially planar region that could be used to determine the location, aggregation, motions, concentration, or other properties of functionalized fluorophores and/or the analyte in the detection environment (e.g., step 260). A thickness of the substantially planar region containing the sample, analyte, and functionalized fluorophores could be a specified thickness such that individual functionalized fluorophores could be imaged with substantially no overlap.

The method 200 could include adding a fixative to the detection environment. Such an added fixative could be configured to substantially reduce motion of the analyte and of functionalized fluorophores in the detection environment. Such a reduction of motion of elements in the detection environment could allow for imaging of the detection environments using very long exposures (e.g., exposure longer than approximately 100 milliseconds) to generate images with a level of blurring below a specified level. In some examples, the fixative could include agarose, PMMA, polystyrene, or some other fixative substance that is compatible with the contents of the sample and/or the detection environment. The sample containing the analyte and/or some other medium added to the sample and/or to the detection environment could be an aqueous medium. The method 200 could include adding aqueous or non-aqueous media or solvents, buffers, auto-fluorescent substances, fixatives, buffers, stabilizers, or other substances or elements to the sample and/or the detection environment according to an application.

The method 200 could further include determining information about the analyte in the detection environment. For example, the method 200 could include determining the location of individual instances of the analyte based on determining which individual functionalized fluorophores are bound to the analyte 260. The method 200 could further include determining, based on determined locations of individual instances of the analyte above, a presence of the analyte in the detection environment, a count of instances of the analyte in the detection environment, a concentration of the analyte in the detection environment, or some other information about the analyte in the detection environment. In examples where the analyte is extracted from some environment of interest, the method 200 could include determining a property of the analyte in the environment of interest based on a determined property of the analyte in the detection environment. For example, a concentration of the analyte in the environment of interest could be determined based on a determined concentration and/or number of instances of the analyte in the detection environment and a dilution of the extracted analyte in the detection environment (e.g., a ration of the volume of sample containing the analyte that is extracted from the environment of interest and a volume of the detection environment and/or of a medium in the detection environment). Other additional and/or alternative elements of the method 200 are anticipated.

The example embodiments described herein can use a single variety of functionalized fluorophore used to image and/or determine one or more properties of an analyte in an environment and/or in a sample extracted from an environment. However, more than one type of functionalized fluorophore could be used to determine one or more properties of more than one respective analyte in an environment. Additionally or alternatively, one or more of the respective analytes could be components of an analyte of interest, e.g., the analyte of interest could be a cancer cell and respective analytes could be unique markers on the surface of the cancer cell. One or more properties of the analyte of interest could be determined based on information about the respective analytes determined from information about respective functionalized fluorophores.

IV. Example Devices

Figure 3:
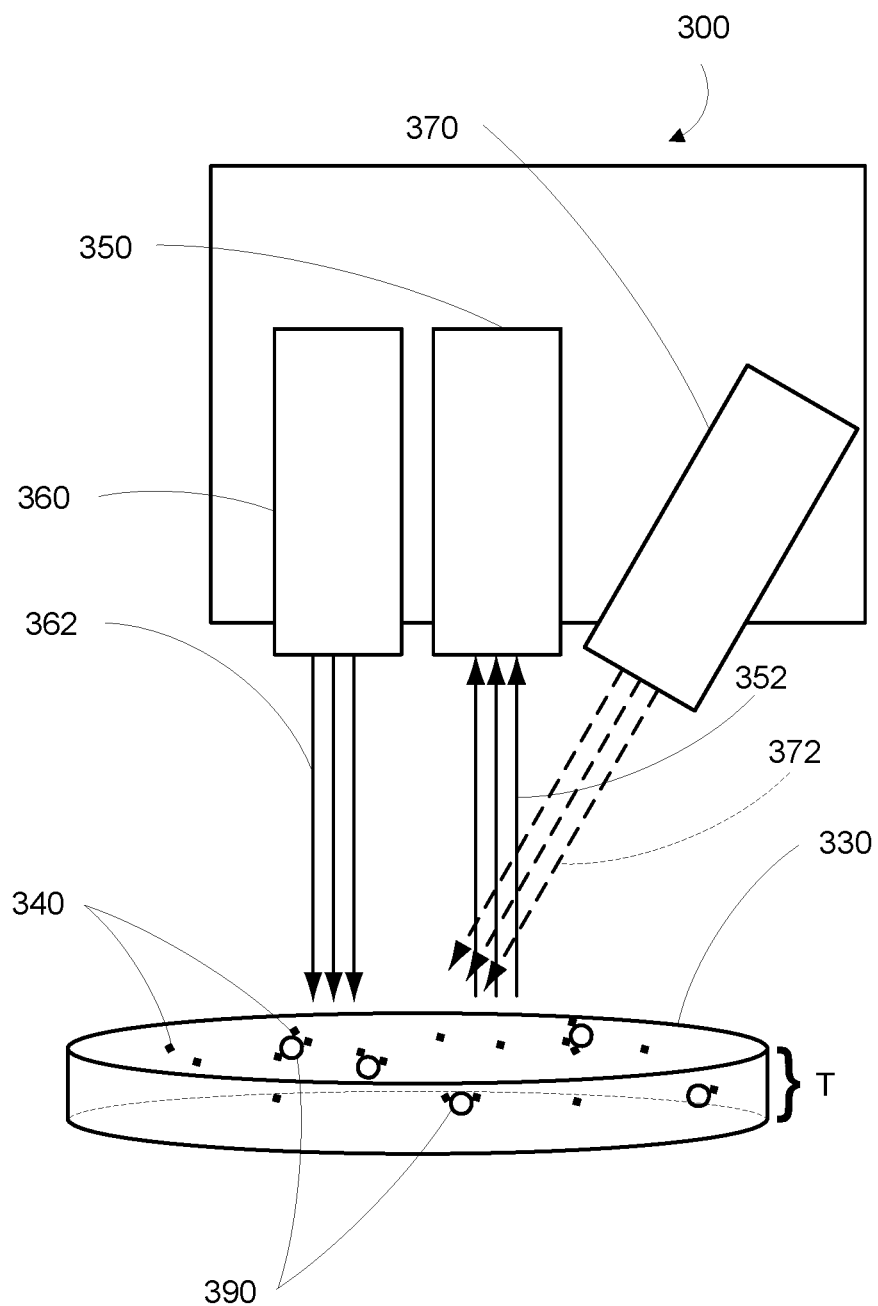
FIG. 3 is a perspective view of an example device.

A device 300 as illustrated in FIG. 3 can determine one or more properties of an analyte 390 in a detection environment 330 by interrogating functionalized fluorophores 340 in the detection environment 330. The detection environment 330 can be any environment containing analytes of interest 390 such that functionalized fluorophores 340 in the detection environment 330 can selectively interact with the analyte of interest 390 and such that the functionalized fluorophores 340 can be excited by illumination 362 from a light source 360 of the device 300 and emitted light 352 emitted by the functionalized fluorophores 330 in response to the illumination 362 can be detected by a light sensor 350 of the device 300. Further, the functionalized fluorophores 440 have a fluorescent property that can be modulated by a modulating field 372 produced by a fluorescence modulator 370.

The detection environment 330 could include a biological tissue (e.g., a tissue of a living human, animal, plant, a fluid or other portion of a lake, river, or stream, etc.). The detection environment 330 could be a sample in a sample container, cuvette, pipette, microscope slide, or other vessel. The detection environment 330 could be part of a biological or chemical process. For example, the detection environment 330 could be a fluid in a water treatment process, a fluid in a food or drug preparation process, a lake, stream, or river in a natural environment, or some other environment. Additionally or alternatively, contents of the detection environment (e.g., analyte 390) could be extracted from such environments (e.g., the analyte could be extracted from blood in a lumen of vasculature of a living body). The detection environment 330 could be a liquid, a gel, a solid, or some other phase of matter or combination of phases (e.g., an emulsion). The environment 330 could include biological or other samples that had been freeze-dried, desiccated, frozen, vaporized, alkalated, or otherwise prepared, including adding the functionalized nanodiamonds 340 to the detection environment 330.

The detection environment 330 could include a fixative configured to reduce motion of instances of the analyte 390 and of the functionalized fluorophores 340. In some examples, the fixative could include agarose, PMMA, polystyrene, or some other fixative substance that is compatible with the contents of the detection environment 330. A sample containing the analyte and/or some other medium added to the detection environment 330 could be an aqueous medium. A illustrated in FIG. 3, the detection environment 330 is a substantially planar region having a specified thickness, T, such that interrogation of the functionalized fluorophores 340 (e.g., using the light sensor 350 to image emitted light 352 emitted by the functionalized fluorophores 330 in response to the illumination 362) could generate sufficient information to determine the location of substantially all individual instances of the analyte 390 in the detection environment based on a determination of which functionalized fluorophores 340 in the detection environment 330 are bound to the analyte 390. For example, the thickness, T, of the substantially planar detection environment 330 could be between approximately 10 microns and approximately 20 microns. Further, a concentration and/or count of the analyte 390 in the detection environment 330 and/or an environment from which the analyte was extracted could be determined based on the determined locations of individual instances of the analyte 390 in the detection environment 330.

The light sensor 350 may include any elements capable of detecting at least one property of emitted light 352 emitted by the functionalized fluorophores 340 in response to exposure to illumination 362 from the light source 360, which could include any properties that may relate to the location, state of binding with the analyte, orientation, or other properties of the functionalized fluorophores 340 and/or the analyte 390. For example, the light sensor 350 could be an imager configured to image emitted light 352 emitted by the functionalized fluorophores 340 in the detection environment 330. In some examples, the light sensor 350 may include one or more active pixel sensors, linear or planar CCDs, photodiodes, image tubes, photomultipliers, photocells, photoresistive elements, cameras, or some other imaging elements or combination of elements.

The light sensor 350 could be configured to receive ultraviolet light, visible light, infrared light, or other types of electromagnetic radiation. Elements of the light sensor 350 could be configured to be selectively sensitive to received light signals having a wavelength within a first specified range of wavelengths (e.g., a range of wavelengths corresponding to an emission spectrum of the functionalized fluorophores 340) and/or selectively insensitive to light signals having a wavelength within a second specified range of wavelengths (e.g., a range of wavelengths corresponding to an emission spectrum of the light source 360). Additionally or alternatively, the light sensor 350 could include one or more filters to block one or more ranges of wavelengths from being received by light-sensitive elements (e.g., photodetectors, photodetector arrays) of the light sensor 350. For example, the functionalized fluorophores 340 could include nanodiamonds containing nitrogen-vacancy defects, and the light sensor 350 could be configured to be sensitive to light signals having wavelengths between approximately 650 nanometers and approximately 800 nanometers (i.e., to wavelengths corresponding to an emission spectrum of nitrogen-vacancy defects in diamond).

The light sensor 350 could include other optical elements (e.g., lenses, apertures, diffraction gratings, filters, dichroic elements, polarizers). For example, the light sensor 350 could include an optical system configured such that the light sensor 350 has a focal plane that is substantially coincident with the substantially planar detection environment 330 (i.e., such that the substantially planar region can be imaged in-focus by the light sensor 350). The light sensor 350, in combination with the light source 360, could be configured in a variety of ways to enable imaging of emitted light 363 emitted by the functionalized fluorophores 340 (e.g., confocal imaging, bright field imaging, dark field imaging, multi-photon imaging).

The device 300 further includes a light source 360 configured to transmit illumination 362 that can penetrate the detection environment 330 to illuminate the functionalized fluorophores 340. The wavelength of the transmitted illumination 362 could be specified to penetrate biological tissues; for example, the transmitted illumination 362 could have a wavelength within a near-infrared (NIR) transparency window of biological tissue. The wavelength of the transmitted illumination 362 could be specified to be a wavelength that causes fluorescence and/or emission of light signals by the functionalized fluorophores 340. In some examples, the functionalized fluorophores 340 could include nanodiamonds containing nitrogen-vacancy defects, and the wavelength of the transmitted illumination 362 could be between approximately 500 and 650 nanometers. The light source 360 could be configured to transmit illumination having a specified polarization, wavelength, intensity, or other property during a first period and to transmit illumination having a different specified polarization, wavelength, intensity, or other property during a second period.

The device 300 also includes a fluorescence modulator 370. The fluorescence modulator 370 may be configured to provide a modulating field 372 in the detection environment 330 to modulate a fluorescent property (e.g., a fluorescence intensity, a polarization of spin states, energy levels of spin states, a fluorescence lifetime, an extinction coefficient, a quantum yield, a degree of polarization-dependence, an orientation of a polarization-selective fluorophore) of the functionalized fluorophores 340. The modulating field 372 could include an electrical field, a magnetic field, an electromagnetic field, and/or electromagnetic radiation. Such operations of the fluorescence modulator 370 could enable a variety of methods of detecting and/or determining properties of the detection environment 330, the functionalized fluorophores 340, and/or the analyte 390. In some examples, the fluorescence modulator 370 could be configured to emit microwave radiation having a specified frequency. In some examples, the fluorescence modulator 370 could be configured to emit electromagnetic radiation configured to affect and/or control the occupancy of one or more spin or other fluorescence-related states of the functionalized fluorophores 340. In some examples, the fluorescence modulator 370 could be configured to direct a DC magnetic field (e.g., by including one or more permanent magnets or electromagnets and associated electronics/actuators) and/or an electric field into the detection environment 330.

The light sensor 350, fluorescence modulator 370, and light source 360 could be configured as illustrated in FIG. 3 (i.e., separate, roughly parallel, non-coaxial) or could be configured in another way, according to an application. In some examples, the light sensor 350 and light source 360 could be coupled to a set of common optical elements to enable some function. For example, the light source 360 and light sensor 350 could each include an aperture and could be optically coupled to a beam splitter and other optics to enable the device 300 to be operated as a confocal microscope. In another example, the light source 360 could include two light sources configured to produce beams of illumination, where the directions of the beams are controllable using some apparatus, for example a set of galvanometer-driven mirrors. The galvanometers could be operated such that functionalized fluorophores 340 in specified regions (where the beams from the light sources overlap) could be illuminated such that functionalized fluorophores 340 in the specified regions emitted light. Other configurations and applications are anticipated.

The device 300 could be configured to enable other imaging modalities and/or to operate in concert with other devices configured to enable other imaging modalities. In some examples, the device 300 could include elements to enable magnetic resonance imaging. In some examples, a magnetic field generator and/or microwave radiation emitter could be used to alter properties of the functionalized fluorophores 340 (e.g., the energy levels, relative population, or other properties of spin or other quantum states of color centers in a nanodiamond of the functionalized fluorophores) in the detection environment 340 to enable other forms of imaging using the functionalized fluorophores 340 and/or to enable the imaging of the analyte 390 in specific regions of the detection environment 330. Additionally or alternatively, the multiple imaging modalities could be used in a complementary fashion to enable some function.

Figure 4:
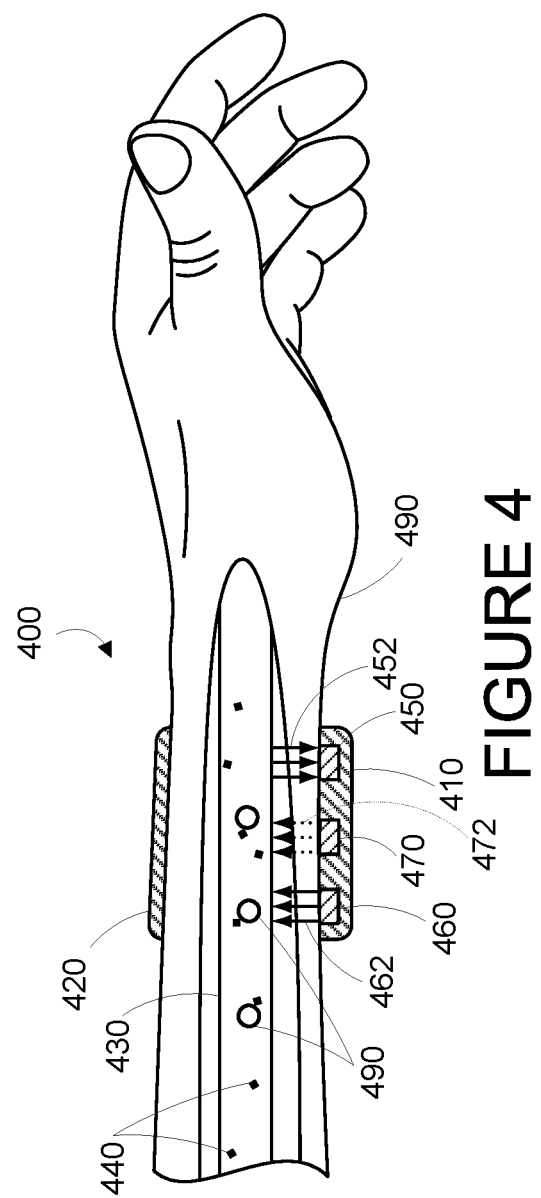
FIG. 4 is side partial cross-sectional view of an example wrist-mounted device, while on a human wrist.

FIG. 4 is a partial cross-sectional side view of a human wrist illustrating the operation of various examples of a wrist-mounted device 400. In the example shown in FIG. 4, the wrist-mounted device 400 includes a measurement platform 410 mounted on a strap or wristband 420 and oriented on the anterior side 490 of the wearer's wrist. Measurement platform 410 is positioned over a portion of the wrist where subsurface vasculature 430 is easily observable. Functionalized fluorophores 440 have been introduced into a lumen of the subsurface vasculature 430 (e.g., by injection, ingestion, etc.). In this example, measurement platform 410 includes a data collection system having a light sensor 450, a light source 460, and a fluorescence modulator 470. The functionalized fluorophores 440 are configured to selectively interact with (e.g., bind to) an analyte 490 in the subsurface vasculature 430.

The state of the subsurface vasculature 430 during detection is illustrated in FIG. 4. At this time, light source 460 is transmitting illumination 462 into the portion of subsurface vasculature 430 and light sensor 450 is detecting an emitted light 452 emitted by the functionalized fluorophores 440 in response to the illumination 462. Additionally, the fluorescence modulator 470 is producing a modulating field 472 to modulate a fluorescent property of the functionalized fluorophores 440.

The wrist-mounted device 400 could be operated to interrogate the functionalized fluorophores 440 to determine information about the functionalized fluorophores 440, the analyte 490, the portion of subsurface vasculature 430, a health state of the wearer, or some other information. For example, the wrist-mounted device 400 could be operated to determine the location, count, concentration, or other information about the analyte 490 based on determining the location of functionalized fluorophores 440 in the portion of vasculature 430 and further determining which functionalized fluorophores 440 are bound to the analyte.

The elements of the wrist-mounted device 400 (e.g., light sensor 450, light emitter 460, electromagnetic field emitter) could additionally or alternatively be operated to enable a variety of methods for detecting and/or determining properties of the subsurface vasculature 430, the functionalized nanodiamonds 440, the functionalized magnetic particles 480, and/or the analyte 490. The methods implemented could be similar to those described herein. Other methods of detection and/or determination are anticipated.

FIG. 4 illustrates paths of the transmitted illumination 462 transmitted by the light source 460, the modulating field 472 produced by the fluorescence modulator 470, and the emitted light 452 detected by the light sensor 450 that do not overlap. However, in some instances, the light source 460, fluorescence modulator 470, and/or the light sensor 450 may be angled towards each other so that they are illuminating and sensing from essentially the same area of subsurface vasculature 430. Other configurations of light sources, light sensors, fluorescence modulators, light paths, directed energy fields, and other elements are anticipated. Further, it is anticipated that more than one light source, field generator, or light sensor may be included to enable the embodiments and methods disclosed herein.

Figure 5:
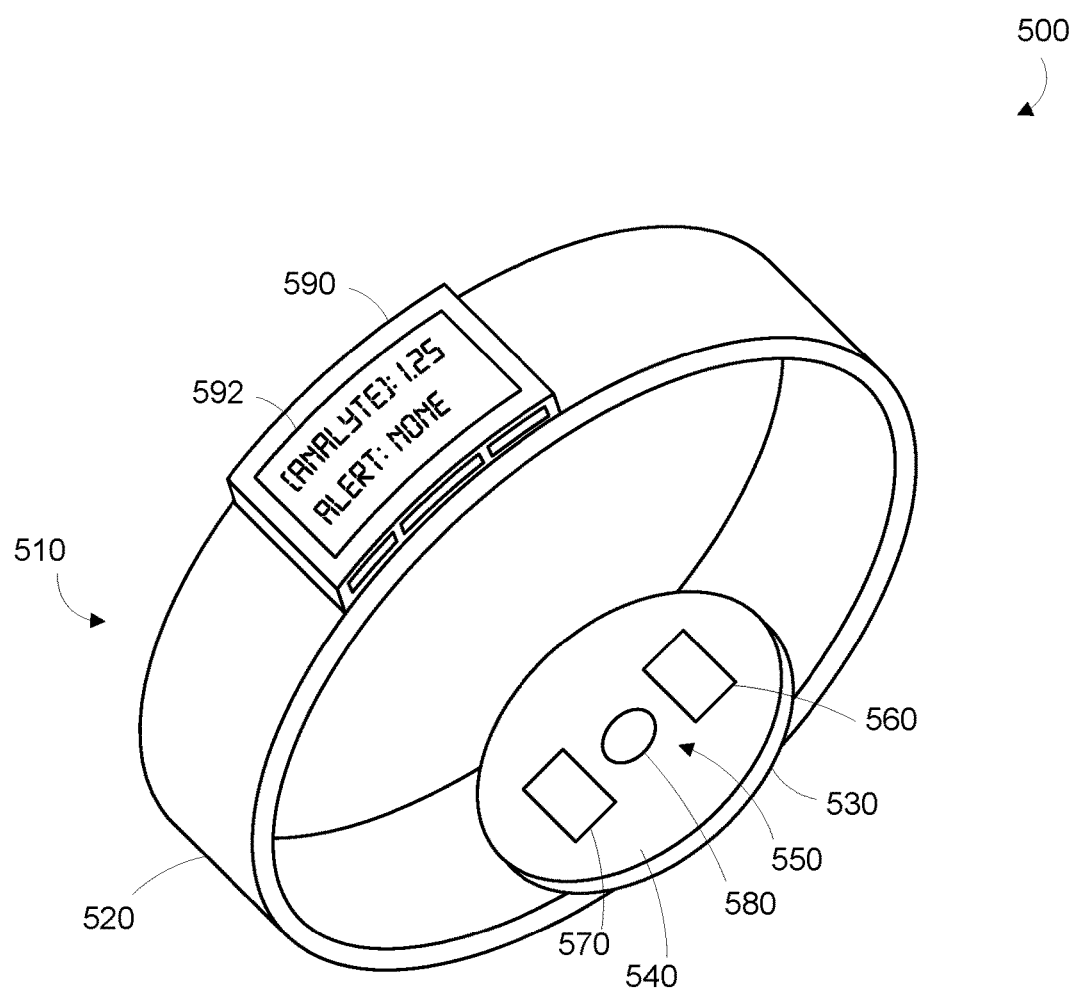
FIG. 5 is a perspective view of an example wearable device.

A wearable device 500 (illustrated in FIG. 5) can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other tissues or environments of interest are easily observable, the qualification of which will depend on the type of detection system used. The device may be placed in close proximity to the skin or tissue, but need not be touching or in intimate contact therewith. A mount 510, such as a belt, wristband, ankle band, etc. can be provided to mount the device at, on or in proximity to the body surface. The mount 510 may prevent the wearable device from moving relative to the body to reduce measurement error and noise. In one example, shown in FIG. 5, the mount 510, may take the form of a strap or band 520 that can be worn around a part of the body. Further, the mount 510 may be an adhesive substrate for adhering the wearable device 500 to the body of a wearer.

A measurement platform 530 is disposed on the mount 510 such that it can be positioned on the body where subsurface vasculature is easily observable. An inner face 540 of the measurement platform is intended to be mounted facing to the body surface. The measurement platform 530 may house a data collection system 550, which may include at least one detector 560 for detecting at least one physiological parameter, which could include any parameters that may relate to the health of the person wearing the wearable device. For example, the detector 560 could be configured to measure blood pressure, pulse rate, respiration rate, skin temperature, etc. In a non-exhaustive list, detector 560 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 550 may be miniaturized so that the wearable device may be worn on the body without significantly interfering with the wearer's usual activities.

At least one of the detectors 560 is a light sensor configured to detect light emitted by functionalized fluorophores in blood circulating in subsurface vasculature proximate to the wearable device 500. The light sensor could be a photodiode, a photomultiplier, a CCD, a photocell, a photoresistive element, a camera, or any other sensor or sensors configured to detect light emitted by the functionalized fluorophores.

The functionalized fluorophores can emit light in response to illumination. Further, the functionalized fluorophores have a fluorescent property that is modulatable. The light sensor could include a filter that is configured to substantially block light emitted by a light source 570 of the data collection system 550.

The data collection system 550 further includes a light source 570 for transmitting illumination that can penetrate the wearer's skin into the portion of subsurface vasculature, for example, into a lumen of the subsurface vasculature. The transmitted illumination can be any kind of illumination that is benign to the wearer and that results at least in absorption of light energy by the functionalized fluorophores proximate to the light source 570. The wavelength of the transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission the functionalized fluorophores. In some examples, the functionalized fluorophores could include nanodiamonds containing negatively-charged nitrogen vacancy centers, and the wavelength of the transmitted illumination could be between approximately 500 and 650 nanometers. The light source 570 could be configured to produce additional or alternative illumination that results in emission of light by other chemicals, imaging agents, biological elements, or other analytes proximate to the light source 570.

A fluorescence modulator 580 may also be included in the data collection system 550. In such embodiments, the fluorescence modulator 580 may be configured to emit and/or produce a variety of electrical, magnetic, and/or electromagnetic fields or other energies into the portion of subsurface vasculature to enable a variety of methods of detecting and/or determining properties of the portion of subsurface vasculature, functionalized fluorophores, and/or analytes proximate to the device 500. In some examples, the fluorescence modulator 580 could be configured to emit microwave radiation having a specified frequency. In some examples, the fluorescence modulator 580 could be configured to emit electromagnetic radiation configured to affect and/or control the occupancy of one or more spin or other quantum states of one or more color centers contained in nanodiamonds of the functionalized fluorophores. In some examples, the fluorescence modulator 580 could be configured to produce a DC magnetic and/or electric field.

The wearable device 500 may also include a user interface 590 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 590 may include a display 592 where a visual indication of the alert or recommendation may be displayed. The display 592 may further be configured to provide an indication of the measured physiological parameters, for instance, the concentrations of certain blood analytes being measured.

Figure 6A:
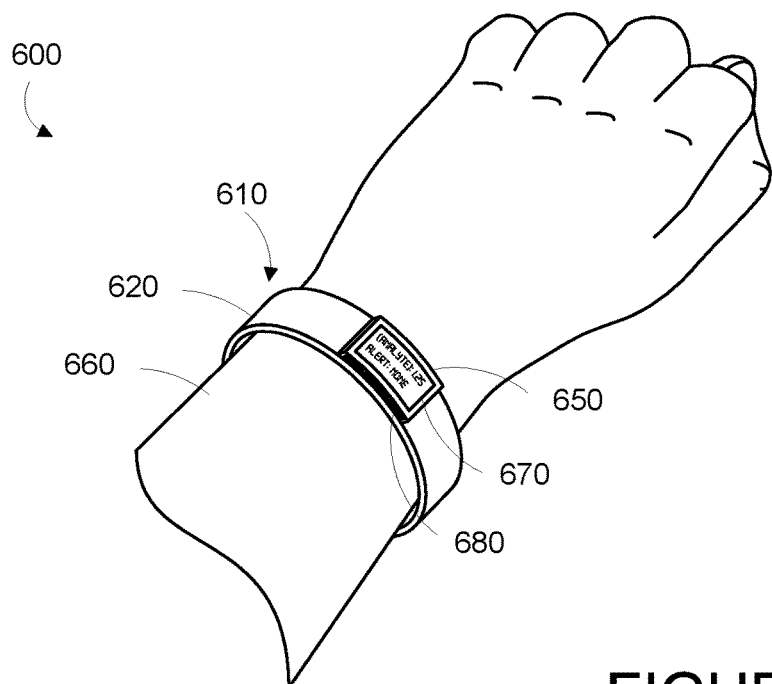
FIG. 6A is a perspective top view of an example wrist-mounted device, when mounted on a wearer's wrist.
Figure 6B:
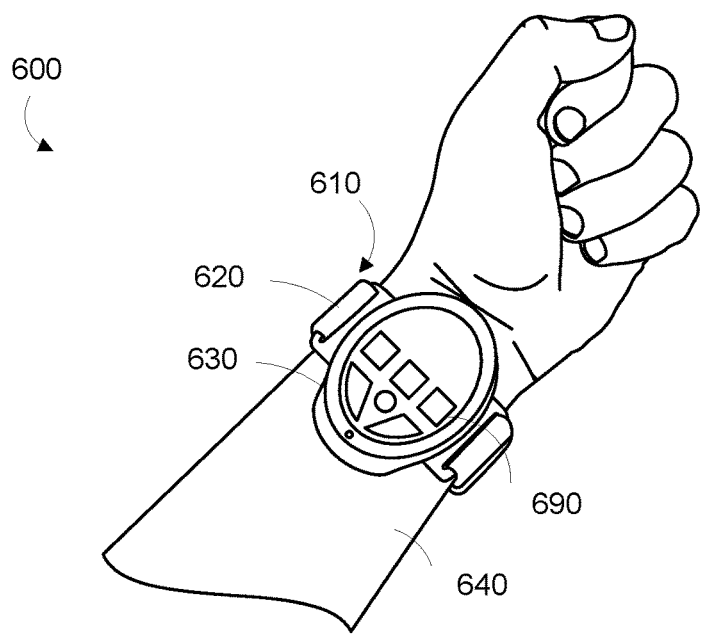
FIG. 6B is a perspective bottom view of an example wrist-mounted device shown in FIG. 6A, when mounted on a wearer's wrist.

In some examples, the wearable device is provided as a wrist-mounted device, as shown in FIGS. 6A and 6B. The wrist-mounted device may be mounted to the wrist of a living subject with a wristband or cuff, similar to a watch or bracelet. As shown in FIGS. 6A and 6B, the wrist mounted device 600 may include a mount 610 in the form of a wristband 620, a measurement platform 630 positioned on the anterior side 640 of the wearer's wrist, and a user interface 650 positioned on the posterior side 660 of the wearer's wrist. The wearer of the device may receive, via the user interface 650, one or more recommendations or alerts generated either from a remote server or other remote computing device, or alerts from the measurement platform. Such a configuration may be perceived as natural for the wearer of the device in that it is common for the posterior side 660 of the wrist to be observed, such as the act of checking a wrist-watch. Accordingly, the wearer may easily view a display 670 on the user interface. Further, the measurement platform 630 may be located on the anterior side 640 of the wearer's wrist where the subsurface vasculature may be readily observable. However, other configurations are contemplated.

The display 670 may be configured to display a visual indication of the alert or recommendation and/or an indication of the measured physiological parameters, for instance, the presence or concentrations of certain blood analytes being measured. Further, the user interface 650 may include one or more buttons 680 for accepting inputs from the wearer. For example, the buttons 680 may be configured to change the text or other information visible on the display 670. As shown in FIG. 6B, measurement platform 630 may also include one or more buttons 690 for accepting inputs from the wearer. The buttons 690 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

V. Example Electronics Platform for a Device

Figure 8:
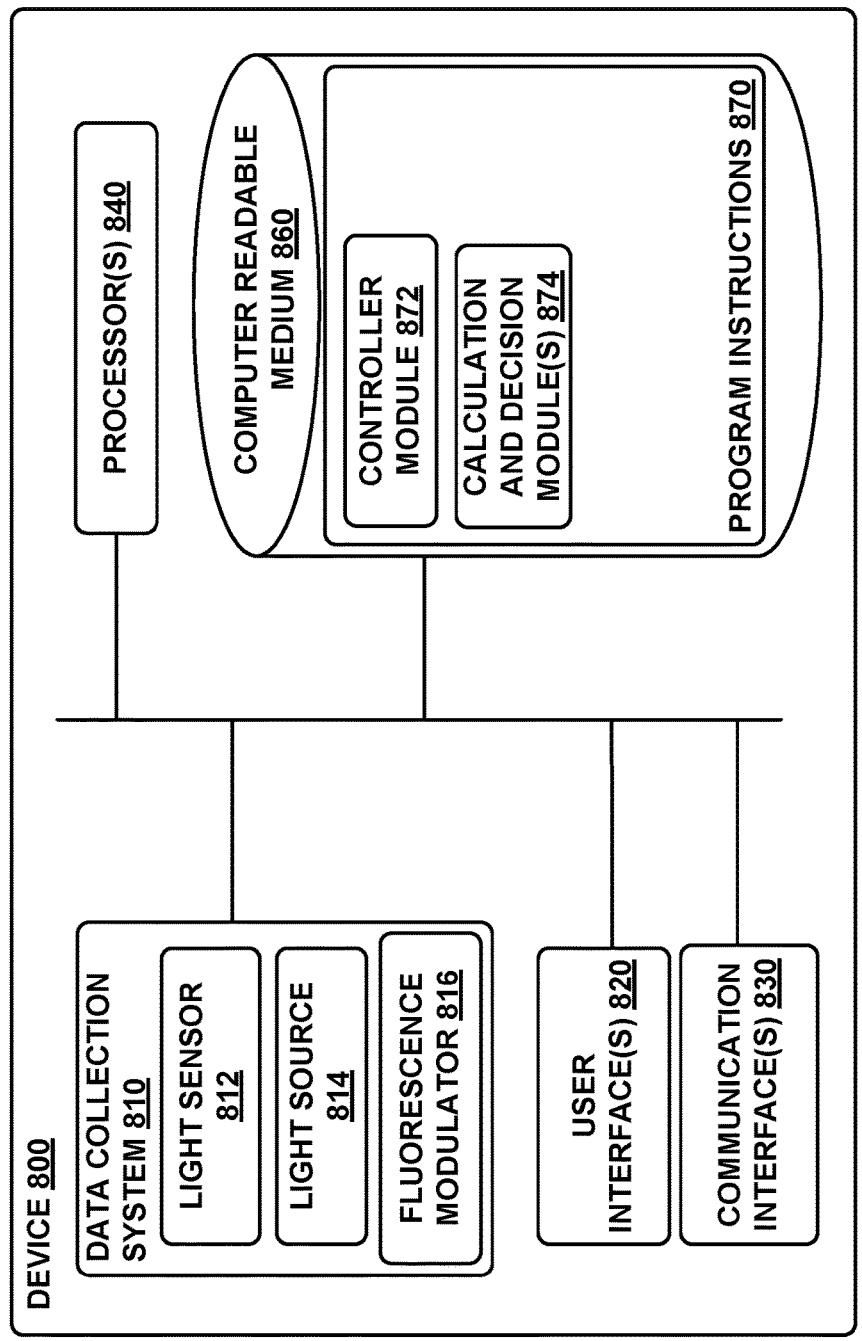
FIG. 8 is a functional block diagram of an example device.

FIG. 8 is a simplified block diagram illustrating the components of a device 800, according to an example embodiment. Device 800 may take the form of or be similar to one of the wrist-mounted devices 400, 500, 600, shown in FIGS. 4, 5, and 6A-B. However, device 800 may also take other forms, such as an ankle, waist, or chest-mounted device. Device 800 could also take the form of a device that is not configured to be mounted to a body. In some examples, device 800 could take the form of a desktop or other analytical device configured to be maintained in proximity to and/or to contain or secure a detection environment (e.g., a sample container, a volume of a water treatment system, a cuvette, a petri dish, a substantially region containing an analyte and functionalized fluorophores) by a frame or other supporting structure, e.g., device 300. For example, device 800 could take the form of a device configured to illuminate and to detect emitted light from an in vitro environment or some controlled laboratory or measurement environment, for example, a fluid volume within a water treatment process.

In particular, FIG. 8 shows an example of a device 800 having a data collection system 810, a user interface 820, communication interface 830 for communicating data to a remote system, and processor(s) 840. The components of the device 800 may be disposed on a mount or on some other structure for mounting the device to enable stable detection of one or more properties of functionalized fluorophores and analytes particles in an environment of interest, for example, to a sample container configured to contain a substantially planar region containing an analyte and functionalized fluorophores.

Processor 840 may be a general-purpose processor or a special purpose processor (e.g., digital signal processors, image processors, graphics processing units (GPUs), application specific integrated circuits, etc.). The one or more processors 840 can be configured to execute computer-readable program instructions 870 that are stored in the computer readable medium 860 and that are executable to provide the functionality of a device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes a light sensor 812, a light source 814, and a fluorescence modulator 816. As described above, the light sensor 812 may include any elements capable of detecting at least one property of light signals emitted by functionalized fluorophores in response to illumination by the light source 814, which could include any properties that may relate to the location, state of binding with the analyte, orientation, or other properties of the functionalized fluorophores and/or the analyte. For example, the light sensor 812 could be an imager configured to image light signals received from functionalized fluorophores in a detection environment. In some examples, the light sensor 812 may include one or more active pixel sensors, linear or planar CCDs, photodiodes, image tubes, photomultipliers, photocells, photoresistive elements, cameras, or some other imaging elements or combination of elements.

The light sensor 812 could be configured to receive ultraviolet light, visible light, infrared light, or other types of electromagnetic radiation. Elements of the light sensor 812 could be configured to be selectively sensitive to received light signals having a wavelength within a first specified range of wavelengths (e.g., a range of wavelengths corresponding to an emission spectrum of a functionalized fluorophore) and/or selectively insensitive to light signals having a wavelength within a second specified range of wavelengths (e.g., a range of wavelengths corresponding to an emission spectrum of the light source 814). Additionally or alternatively, the light sensor 812 could include one or more filters to block one or more ranges of wavelengths from being received by light-sensitive elements (e.g., photodetectors, photodetector arrays) of the light sensor 812. For example, the functionalized fluorophores could include nanodiamonds containing nitrogen-vacancy defects, and the light sensor 812 could be configured to be sensitive to light signals having wavelengths between approximately 650 nanometers and approximately 800 nanometers (i.e., to wavelengths corresponding to an emission spectrum of nitrogen-vacancy defects in diamond).

The light sensor 812 could include other optical elements (e.g., lenses, apertures, diffraction gratings, filters, dichroic elements, polarizers). For example, the light sensor 812 could include an optical system configured such that the light sensor 812 has a focal plane that is substantially coincident with a substantially planar region containing the analyte and functionalized fluorophores (i.e., such that the substantially planar region can be imaged in-focus by the light sensor 812). The light sensor 812, in combination with the light source 814, could be configured in a variety of ways to enable imaging of light signals emitted by the functionalized fluorophores (e.g., confocal imaging, bright field imaging, dark field imaging, multi-photon imaging).

The data collection system 810 further includes a light source 814 configured to transmit illumination that can penetrate the environment of interest to illuminate the functionalized fluorophores. The wavelength of the transmitted illumination could be specified to penetrate biological tissues; for example, the transmitted illumination could have a wavelength within a near-infrared (NIR) transparency window of biological tissue. The wavelength of the transmitted illumination could be specified to be a wavelength that causes fluorescence and/or emission of light signals by the functionalized fluorophores. In some examples, the functionalized fluorophores could include nanodiamonds containing nitrogen-vacancy defects, and the wavelength of the transmitted illumination could be between approximately 500 and 650 nanometers. The light source 814 could be configured to transmit illumination having a specified polarization, wavelength, intensity, or other property during a first period and to transmit illumination having a different specified polarization, wavelength, intensity, or other property during a second period.

A fluorescence modulator 816 is also included in the data collection system 810. The fluorescence modulator 816 may be configured to direct an electrical, magnetic, and/or electromagnetic field into the environment to modulate a variety of fluorescent properties (e.g., a fluorescence intensity, a polarization of spin states, energy levels of spin states, a fluorescence lifetime, an extinction coefficient, a quantum yield, a degree of polarization-dependence, an orientation of a polarization-selective fluorophore) of the functionalized fluorophores. Such operations of the fluorescence modulator 816 could enable a variety of methods of detecting and/or determining properties of the environment, the functionalized fluorophores, and/or analytes. In some examples, the fluorescence modulator 816 could be configured to emit microwave radiation having a specified frequency. In some examples, the fluorescence modulator 816 could be configured to emit electromagnetic radiation configured to affect and/or control the occupancy of one or more spin or other fluorescence-related states of the functionalized fluorophores. In some examples, the fluorescence modulator 816 could be configured to emit a DC magnetic field (e.g., by including one or more permanent magnets or electromagnets and associated electronics/actuators). In some examples, the fluorescence modulator 816 could be configured to emit an electric field.

The program instructions 870 stored on the computer readable medium 860 may include instructions to perform any of the methods described herein. For instance, in the illustrated embodiment, program instructions 870 include a controller module 872, a calculation and decision module 874.

The controller module 872 can include instructions for operating the data collection system 810, for example, the light sensor 812, light source 814, and fluorescence modulator 816. In particular, the controller module 872 can include instructions for operating the light source 814 to emit illumination into a detection environment (e.g., a biological sample container) and controlling the light sensor 812 to detect light signals emitted by the functionalized fluorophores in the environment being interrogated by the device 800 during two or more periods of time. The controller module 872 can further include instructions to operate the fluorescence modulator 816 to modulate a fluorescent property of the functionalized fluorophores in the environment during one or more of the two or more periods of time.

The controller module 872 can also include instructions for operating a user interface 820. For example, controller module 872 may include instructions for displaying data collected by the data collection system 810 and analyzed by the calculation and decision module 874. Further, controller module 872 may include instructions to execute certain functions based on inputs accepted by the user interface 820, such as inputs accepted by one or more buttons or touch interfaces disposed on the user interface.

Communication platform 830 may also be operated by instructions within the controller module 872, such as instructions for sending and/or receiving information via a wireless or wired network interface, which may be disposed on or in the device 800. The communication interface 830 can optionally include one or more oscillators, mixers, frequency injectors, etc. to modulate and/or demodulate information on a carrier frequency to be transmitted and/or received by an antenna. In some examples, the device 800 is configured to transmit and received information from a remote server via the internet (e.g., calibration information regarding the operation of the device 800 to detect properties of an analyte in an environment containing the functionalized fluorophores).

Calculation and decision module 874 may include instructions for receiving data from the data collection system 810, analyzing the data to determine the location, state of binding with the analyte, orientation, or other properties of the functionalized fluorophores, quantifying a measured parameter(s), such as concentration and/or number of a target analyte, analyzing the data to determine if a medical condition is indicated, or other analytical processes relating to the detection environment of the device 800. In particular, the calculation and decision module 874 may include instructions for determining whether individual functionalized fluorophores in the detection environment are bound to the analyte based on the detected light signals emitted from the functionalized fluorophores in response to illumination. This determination could be based on difference images determined by subtracting a fluorescent image of the detection environment (i.e., an image of light received from the environment (including light signals from the functionalized fluorophores) in response to illumination by the light source 814) taken when the fluorescence modulator 816 is not modulating a fluorescence property (e.g., a fluorescence intensity) of the functionalized fluorophores from a fluorescent image of the detection environment taken when the fluorescence modulator 816 is modulating the fluorescence property of the functionalized fluorophores. The calculation and decision module 874 may further include instructions for determining a concentration, count, or other property of the analyte based on the above determination.

The calculation and decision module 874 including instructions for determining whether individual functionalized fluorophores in the detection environment are bound to the analyte could include determining the location of individual functionalized fluorophores, and further determining the location of instances of the analyte and/or determining which of the individual functionalized fluorophores are bound to the analyte based on a determined proximity between individual functionalized fluorophores (e.g., unbound functionalized fluorophores could be less likely to be proximate to other unbound functionalized fluorophores, while functionalized fluorophores that are bound to an instance of the analyte are likely to be within a specified distance (e.g., a distance related to a characteristic size of the analyte) of other individual functionalized fluorophores). Additionally or alternatively, determining whether individual functionalized fluorophores in the detection environment are bound to the analyte could include determining a degree of blur in one or more image of individual functionalized fluorophores and further determining that an individual functionalized fluorophore is bound to the analyte based on the corresponding determined degree of blur (e.g., unbound functionalized fluorophores could have faster characteristic motions in the environment than bound functionalized fluorophores (due, e.g., to a drag, mass, or other property of the analyte) and the faster characteristic motion could cause blurring of a corresponding image of the unbound functionalized fluorophore). Additional methods of determining that individual functionalized fluorophores are bound to the analyte based on light signals detected by the light sensor 812 in response to illumination of an environment by the light source 814 and the operation of the fluorescence modulator 816 are anticipated.

The program instructions of the calculation and decision module 874 may, in some examples, be stored in a computer-readable medium and executed by a processor located external to the device 800. For example, the device 800 could be configured to detect information about a detection environment (e.g., information about detected light signals emitted from functionalized fluorophores in response to illumination) and then transmit the data to a remote server, which may include a mobile device, a personal computer, the cloud, or any other remote system, for further processing.

The computer readable medium 860 may further contain other data or information, such as medical and health history of a user of the device 800, calibration data related to the operation of the device 800, or other information that may be useful in making some determination (e.g., determining a concentration or other property of an analyte in a detection environment and/or in some other environment from which the analyte is extracted, determining whether a medical condition is indicated, determining a medical treatment). Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for users of the device 800 based on data collected over a certain number of measurements (e.g., a certain number of measurements of analyte concentration in samples extracted from a user and detected (in the sample) by the device 800). Baselines may also be generated by a remote server and transmitted to the device 800 via the communication interface 830. The calculation and decision module 874 may also, upon determining that a medical condition is indicated, generate one or more recommendations for the user of the device 800 based, at least in part, on consultation of a clinical protocol. Such recommendations may alternatively be generated by the remote server and communicated to the device 800.

In some examples, the collected physiological parameter data, baseline profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while imaging agents, devices, systems, methods, and other embodiments are described herein by way of example as being employed to detect properties of one or more analytes in in vitro or other detection environments, it is noted that the disclosed imaging agents, devices, systems, and methods can be applied in other contexts as well. For example, detection systems configured to detect one or more properties of an analyte using an imaging agent as disclosed herein may be included in wearable (e.g., body-mountable) and/or implantable devices. In some contexts, such a detection system is situated to be substantially encapsulated by bio-compatible polymeric material suitable for being in contact with bodily fluids and/or for being implanted. Such body-mounted and/or implanted detection systems can include circuitry configured to operate light emitters, light sensors, microwave emitters, magnetic field emitters, or other elements to enable detection of properties of an analyte by detecting one or more properties of an imaging agent configured to selectively bind to the analyte.

In other examples, imaging agents, devices, systems, and methods disclosed herein may be applied to measure properties of one or more analytes in and/or extracted from environments that are not in or on a human body. For example, detection systems disclosed herein may be employed to measure analyte properties in a fluid of an animal, where the analyte is extracted from the fluid of the animal and introduced, in combination with an imaging agent as described herein, to a detection environment. In another example, imaging agents, devices, systems, and methods disclosed herein may be applied to measure properties of an analyte extracted from an environmental fluid, such as a fluid in a river, lake, marsh, reservoir, water supply, sanitary sewer system, or storm sewer system. In another example, imaging agents, devices, systems, and methods disclosed herein may be applied to measure properties of an analyte extracted from a fluid that is part of a process, such as a waste treatment process, pharmaceutical synthesis process, food preparation process, fermentation process, or medical treatment process Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a light source;
   a light sensor;
   a fluorescence modulator;
   a detection environment; and
   a controller that is operably coupled to the light sensor, the light source, and the fluorescence modulator and that is operable to perform controller operations comprising:
   using the light source to expose the detection environment to first illumination during a first period of time, wherein the detection environment includes a plurality of functionalized fluorophores, wherein each of the functionalized fluorophores has a fluorescent property that is modulatable, wherein each of the functionalized fluorophores is functionalized to selectively bind to an analyte, and wherein the first illumination causes individual functionalized fluorophores to emit respective first-period signals;
   using the light sensor to detect the first-period signals emitted by the functionalized fluorophores during the first period of time in response to the first illumination;
   using the fluorescence modulator to modulate the modulatable fluorescent property of the functionalized fluorophores during a second period of time;
   using the light source to expose the detection environment to second illumination during the second period of time, wherein the second illumination causes individual functionalized fluorophores to emit respective second-period signals;
   using the light sensor to detect the second-period signals emitted by the functionalized fluorophores during the second period of time in response to the second illumination; and
   determining which individual functionalized fluorophores in the plurality of functionalized fluorophores are bound to the analyte based at least on the detected first-period signals and the detected second-period signals, wherein the determining is further based on at least one characteristic that distinguishes between bound and unbound functionalized fluorophores.

2. The system of claim 1, wherein the fluorescence modulator comprises a microwave emitter, wherein the microwave emitter is configured to expose the detection environment to microwave radiation.

3. The system of claim 1, wherein each of the functionalized fluorophores comprises at least one nanodiamond comprising at least one nitrogen-vacancy defect, wherein the light source is configured to emit light having wavelengths in the range of about 500 nanometers to about 650 nanometers into the detection environment, and wherein the light sensor is configured to detect light having wavelengths in the range of about 650 nanometers to about 800 nanometers.

4. The system of claim 3, wherein the fluorescence modulator comprises a magnet, wherein the magnet is configured to expose a region of the detection environment to a high-strength magnetic field.

5. The system of claim 1, wherein each of the functionalized fluorophores comprises at least one quantum dot.

6. The system of claim 1, wherein the controller operations further comprise:
   determining locations of individual instances of the analyte in the detection environment based on determining which individual functionalized fluorophores in the plurality of functionalized fluorophores are bound to the analyte.

7. The system of claim 6, wherein the controller operations further comprise:
   determining a concentration of the analyte based on determining the locations of individual instances of the analyte in the detection environment.

8. The system of claim 1, wherein determining which individual functionalized fluorophores in the plurality of functionalized fluorophores are bound to the analyte comprises determining a degree of blurring of images of the individual functionalized fluorophores, wherein the images of the individual functionalized fluorophores are based on the detected first-period signals and the detected second-period signals.

9. The system of claim 1, wherein determining which individual functionalized fluorophores in the plurality of functionalized fluorophores are bound to the analyte comprises determining that the individual functionalized fluorophores are proximate to other individual functionalized fluorophores based on the detected first-period signals and the detected second-period signals.

10. The system of claim 1, wherein the detection environment is a substantially planar region containing the analyte, the functionalized fluorophores, and a medium containing the analyte and the functionalized fluorophores.

11. The system of claim 10, wherein the substantially planar region has a thickness between approximately 10 microns and approximately 20 microns.

12. The system of claim 10, wherein the medium is an aqueous medium.

13. The system of claim 10, wherein the medium comprises a fixative that is configured to substantially reduce motion of the analyte and the functionalized fluorophores in the detection environment.

14. The system of claim 1, wherein the analyte is a cell.

* * * * *